United States Patent [19]

Triva

[11] Patent Number: 5,627,071
[45] Date of Patent: May 6, 1997

[54] DEVICE FOR SAMPLE COLLECTION AND IN VITRO TRANSPORT, MAINLY FOR DIAGNOSTIC USE

[75] Inventor: Daniele Triva, Bovezzo, Italy

[73] Assignee: Copan Italia S.p.A., Bovezzo, Italy

[21] Appl. No.: 289,447

[22] Filed: Aug. 12, 1994

[30] Foreign Application Priority Data

Sep. 9, 1993 [IT] Italy .................................. MI93A1934

[51] Int. Cl.$^6$ .................................................. C12M 3/00
[52] U.S. Cl. ........................... 435/307.1; 435/309.1; 435/309.2; 422/102; 436/810
[58] Field of Search ........................ 435/307.1, 309.1, 435/309.2; 422/102; 436/810

[56] References Cited

U.S. PATENT DOCUMENTS 4,877,036 10/1989 Saint-Amand ........................ 128/749

FOREIGN PATENT DOCUMENTS 9008817 9/1990 WIPO.

*Primary Examiner*—David A. Redding
*Attorney, Agent, or Firm*—Henderson & Sturm

[57] ABSTRACT

The invention relates to a device for sample collection and in vitro transport for diagnostic use, of the type comprising a test tube containing transport medium in gel form and a rod bearing at one of its ends a cap for sealing said test tube and, at its opposite end, means for collecting said sample to be dipped into said transport medium, characterized in that said test tube has an essentially cylindrical shape interrupted by a neck situated in the nearby of the level reached inside the test tube by the free surface of the transport medium in gel form.

12 Claims, 2 Drawing Sheets

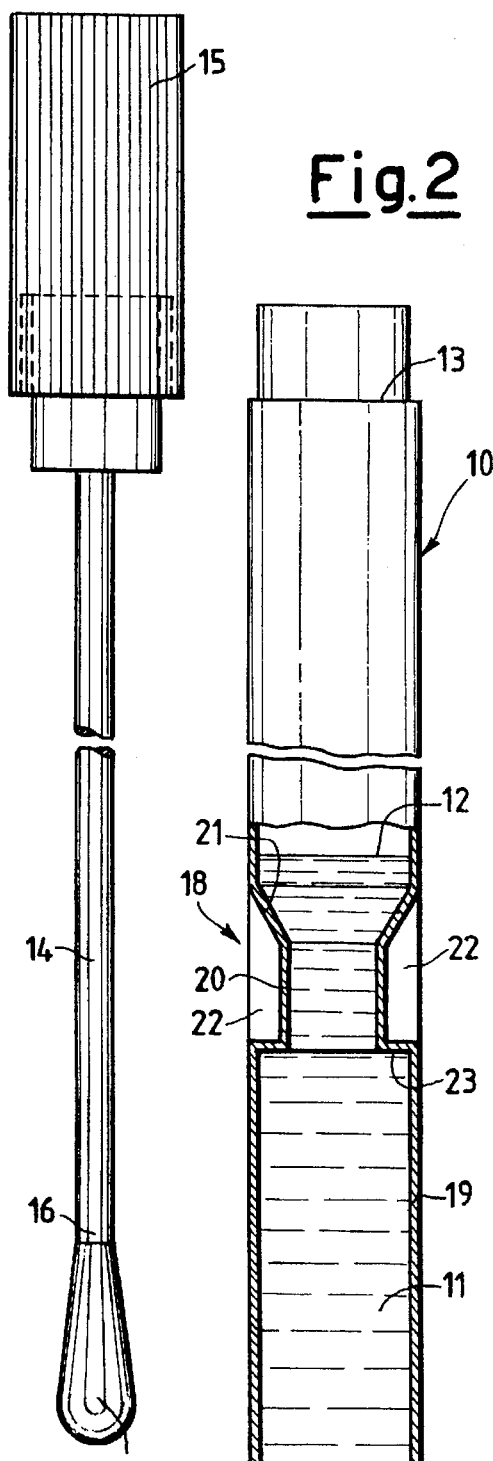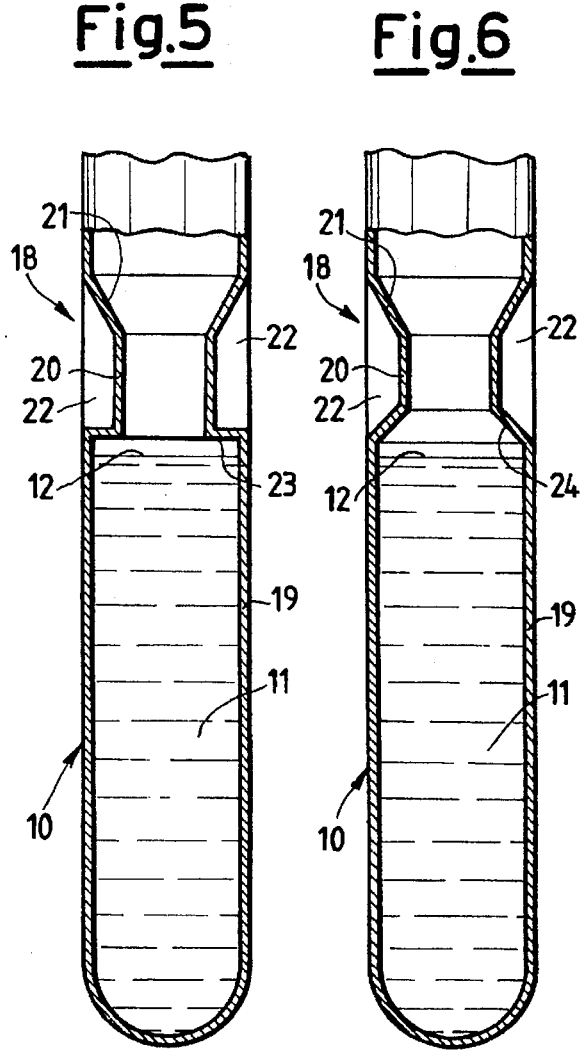

5,627,071

DEVICE FOR SAMPLE COLLECTION AND IN VITRO TRANSPORT, MAINLY FOR DIAGNOSTIC USE

TECHNICAL FIELD

In the field of clinical and diagnostic tests, swabs with transport medium for collecting and transporting aerobic and anaerobic microorganisms, are known. In general, these are systems comprised of a collecting rod with a fiberous nose and a test tube which contains, at its bottom, the transport medium, in gel form.

DISCUSSION OF BACKGROUND AND MATERIAL INFORMATION

In the oldest systems, the gel which constitutes the medium is contained inside a glass vial, inside the interior of which the rod is broken after sample collecting.

The nearly total filling of the vial with the medium secures that the swab will be totally dipped inside the gel, even if during its transport, the vial undergoes impacts or overturning.

The poor practicalness of this system, and the contamination risk caused only those systems to be practically successful on the market, in which the sample collection rod is constrained to a plug, so that, after sample collection, the test tube which contains the medium can be closed by the cap provided on the swab rod.

In this way, the rod needs not be fractured after being dipped into the gel. However, the cap system is exposed to the following drawbacks.

During the transport, in particular when it is carried out by mail service, it is very likely that the test tubes suffer shocks and impacts, which may even be considerably strong, such as to cause the gel to get detached from the bottom and the walls of the test tube. The ultimate effect of such an occurrence is that the gel is frangmented into a plurality of particles, with it being consequently possible that the transport medium moves away from the region in which the nose of the sample bearing rod is.

Such a phenomenon of axial flow of the gel inside the test tube can cause the actual gel conditions to diverge, to a determining extent, from the conditions of survival of the microorganisms in the sample, thus causing the test to become unreliable.

One can hence realize how the devices of known type are not capable of securing a permanent and continuous contact between the sample collecting swab and the medium in gel form during the transport, and, therefore, a proper sample storage.

A further problem which conditions the reliability of sample storage derives from the undesired entraining of air bubbles, which is caused by the dipping of the rod which bears the sample into the "column" of gel medium contained inside the test tube.

The formation of these bubbles is very haphazard and depends on gel compactness, on the temperature the gel has at test tube use time, the gel age, the manual skill of the operator. The presence of air bubbles inside the gel, in particular when such bubbles are in the nearby of the sample, changes the aerobic/anaerobic condition of the system, thus potentially compromising the storage capability, in particular of anaerobic microorganisms.

SUMMARY OF INVENTION

The main purpose of the present invention is of solving the above cited problems, in particular as regards the capability of the transport medium in gel form to flow and get fractured, and to the possibility of air bubble formation owing to the entrainment of air by the sample bearing rod when the latter is slid into the interior of the test tube.

In order to accomplish this purpose, as well as still other advantages which will become clearer from the following disclosure, the present invention proposes a device for sample collection and in vitro transport for diagnostic use, of the type comprising a test tube with transport medium in gel form and a rod bearing at one of its ends a cap for sealing said test tube and, at its opposite end, means for collecting said sample to be dipped into said transport medium, characterized in that said test tube has an essentially cylindrical shape interrupted by a neck situated in the nearby of the level reached inside the test tube by the free surface of the transport medium in gel form.

According to a preferred embodiment, such a neck is under the level reached by the free surface of the transport medium inside the test tube.

According to a different embodiment of the invention, such a neck is above the level reached by the surface of the transport medium in gel form.

According to a further embodiment, such a neck essentially consists in a change in the cross section of the test tube caused between a downwards oriented taper, which defines, hence, a separation zone between a longer-radius circular cross-section, and an underlying, shorter-radius circular cross-section along the longitudinal axis of the test tube.

From such a shorter-radius cross-section, the cross-section of the test tube turns back into the original, longer-radius cross-section either sharply on a perpendicular plane to the longitudinal axis of the test tube, or gradually, through an upwards oriented taper.

In order to better disclose the characteristics and advantages of the device according to the present invention, in the following an exemplifying, non-limitative embodiment thereof is disclosed with reference to the figures of the accompanying drawings.

BRIEF DESCRIPTION OF DRAWINGS

In the drawings:

FIG. 2 shows an exploded view of both essential components of the device according to the invention, i.e., the test tube and the rod, in which the test tube is displayed in longitudinal cross-section.

FIG. 5 shows, in an analogous view to the view of FIGS. 2 and 3, a different embodiment of the invention.

FIG. 6 shows, in an analogous view to the view of FIG. 5, a further different embodiment of the invention.

DETAILED DESCRIPTION

Figure 1:
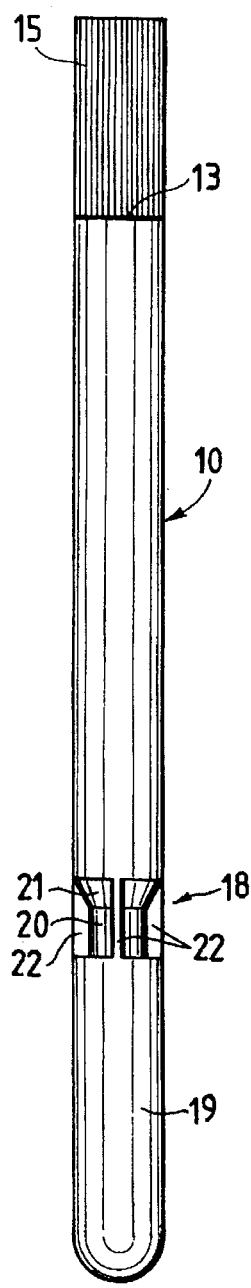
FIG. 1 shows an elevation view of a device according to the present invention.
Figure 3:
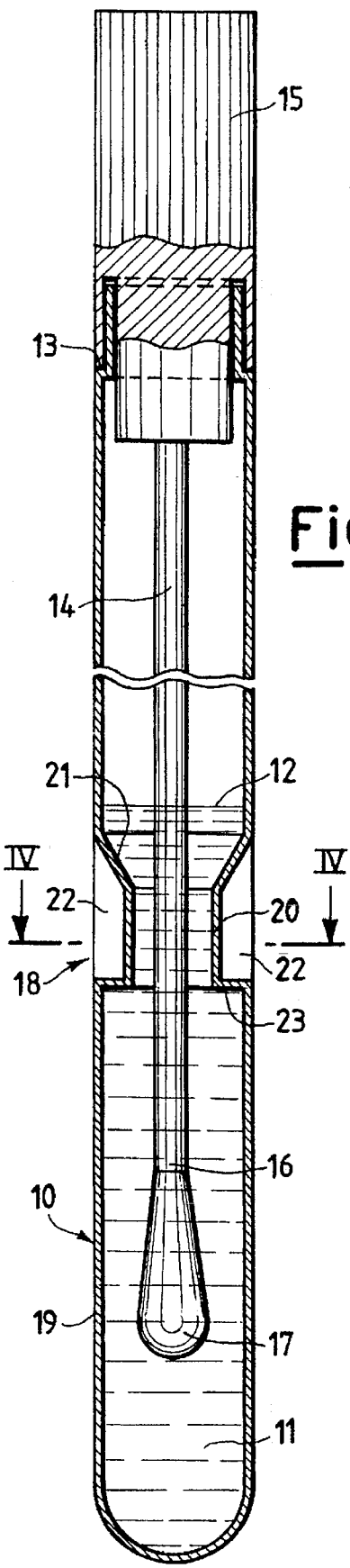
FIG. 3 shows an analogous view to the view of FIG. 2, with both components being coupled with each other in the operating position of the device.
Figure 4:
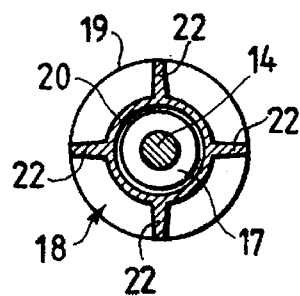
FIG. 4 shows a sectional view taken according to the section line IV—IV of FIG. 3.

Referring to the above Figures, a device according to the invention comprises an essentially cylindrical test tube (10)

which contains a culture medium in gel form (11), displaying a free surface level (12) inside the interior of the test tube.

The upper open end of the test tube is provided with a collar (13) which enables it to receive a sealing means.

The device is completed by a rod (14) bearing, at one of its ends, a cap 15 which precisely performs the task of test tube sealing means, and is hence so shaped, as to be capable of coupling, e.g., in spring-like fashion, with said collar (13) of said test tube.

At its opposite end, the rod (14) is provided with a nose (16) bearing a suitable means, e.g., a fiberous swab (17) for collecting the sample to be analysed.

As said above, the transport medium in gel form is contained inside the test tube (10) up to a free surface level indicated with (12).

In the nearby of such a level (12), the test tube displays a neck (18), in which the circular cross-section (19) of the test tube narrows turning into a shorter-radius cross-section (20), through a downwards-directed conical taper (21), so as to determine a kind of a funnel inside the interior of the test tube. Such a neck is reinforced by ribs (22).

From such a shorter-radius cross-section (20), the cross-section of the test tube (10) suddenly turns back into the original, longer-radius cross-section (19) at a plan (23), perpendicular to the longitudinal axis of the test tube.

According to a different embodiment of the invention, displayed, for exemplifying purposes, in FIG. 6, the shorter-radius cross-section of the test tube can gradually turn back into the longer-radius cross-section, through a taper (24), this time directed upwards.

In FIG. 2, an embodiment of the invention is displayed in which the free surface (12) of the gel medium (11) is at a higher level than the neck (18).

In FIG. 5, a different embodiment of the invention is displayed, in which said free surface (12) is at a lower level than the neck (18).

In both cases, the invention displays the feature of preventing an axial flow of the gel when the test tube containing the collected sample undergoes occasional shocks, e.g., during the transport.

In fact, when, following an impact or a jolt, the gel would tend to flow upwards, towards the high portion of the test tube in the axial direction, losing its compactness and breaking into particles, it would meet the edge (23) of the neck (18), which would oppose such a shift, thus tending to strongly favour the compactness of the same gel, so that the nose of the rod (14) containing the collected sample (17) will continue to remain dipped in the same gel, with no risks that the latter may loose in compactness to create exposed zones—hence, contamination zones, of the collected sample dipped inside the medium.

In the instance of the different embodiment of FIG. 2 in which the neck is under the free surface of the gel, and, hence, is completely immersed inside it, the further advantage is attained, that the formation is prevented of air bubbles when the rod is plunged into the medium.

In fact, the gel volume displacement caused by the rod immersion cannot be transmitted and discharged as an axial displacement of the whole gel column because the neck, which is completely buried inside the gel, prevents such a movement for about ⅔ of the whole cross-section of said cylindrical column. The result is that the air bubbles produced when the rod is plunged into the gel, tend to disappear immediately behind the sample bearing rod nose during the rod plunging into the gel.

As one can realize from the above, the invention make it thus possible the effects to be accomplished, which it aimed at.

A large number of modifications can be supplied to the embodiments of the present invention as disclosed hereinabove for exemplifying, non-limitative purposes, e.g., as regards the precise position of the level of the free surface of the gel medium inside the test tube, and the precise shape of the neck, provided that the principle is met, the neck to be positioned in the nearby of the free surface of the medium.

What is claimed is:

1. An apparatus for sample collection and in vitro transport for diagnostic use, said apparatus comprising a test tube for containing transport medium in gel form; and a rod bearing at one end a cap for sealing said test tube, and, at an opposite end, means for collecting a sample to be dipped into the transport medium, wherein said test tube has an essentially cylindrical shape interrupted by a neck adjacent to a level inside said test tube intended to be reached by a free surface of the transport medium in gel form whereby when said rod is placed into said test tube which contains the transport medium in gel form the means for collecting said sample is dipped into said transport medium, below a level of the free surface of the transport medium.

2. The apparatus according to claim 1, wherein said neck comprises a downwards taper of conical shape from a cylindrical section of said test tube.

3. The apparatus according to claim 1, wherein said neck is provided with strengthening ribs.

4. The apparatus according to claim 1, wherein said neck comprises a change in cross section of said test tube between a downwards oriented taper and an upwards oriented taper.

5. The apparatus according to claim 2, wherein said neck comprises a change in cylindrical cross-section of said test tube, as determined by a downwards-directed conical taper which defines a separation zone between a longer-radius circular cross-section and an underlying shorter-radius circular cross-section along a longitudinal axis of said test tube, with, from said shorter-radius cross-section, the cross-section of said test tube sharply turning back into the initial, longer-radius cross-section on a perpendicular plane to the longitudinal axis of said test tube.

6. The apparatus according to claim 1, wherein said predetermined position of said neck is below the level intended to be reached by the free surface of the transport medium inside the test tube.

7. The apparatus according to claim 1, wherein said predetermined position of said neck is above the level intended to be reached by the free surface of the transport medium inside the test tube.

8. The apparatus according to claim 1, wherein said predetermined position of said neck corresponds substantially to the level intended to be reached by the free surface of the transport medium inside the test tube.

9. The apparatus according to claim 1, further comprising transport medium in gel form contained in said test tube.

10. An apparatus for sample collection and in vitro transport for diagnostic use said apparatus comprising a test tube for containing transport medium in gel form; and a rod bearing at one end a cap for sealing said test tube, and, at an opposite end, means for collecting a sample to be dipped into the transport medium, wherein said test tube has an essentially cylindrical shape interrupted by a neck at a predetermined position relative to a level inside the test tube intended to be reached by a free surface of transport medium in gel form to be contained in said test tube, wherein said neck comprises strengthening ribs.

11. An apparatus for sample collection and in vitro transport for diagnostic use said apparatus comprising a test tube for containing transport medium in gel form; and a rod bearing at one end a cap for sealing said test tube, and, at an opposite end, means for collecting a sample to be dipped into the transport medium, wherein said test tube has an essentially cylindrical shape interrupted by a neck at a predetermined position relative to a level inside the test tube intended to be reached by a free surface of transport medium in gel form, wherein said neck comprises a change in cross section of the test tube between a downwards oriented taper and an upwards oriented taper.

12. An apparatus for sample collection and in vitro transport for diagnostic use said apparatus comprising a test tube for containing transport medium in gel form; and a rod bearing at one end a cap for sealing said test tube, and, at an opposite end, means for collecting a sample to be dipped into the transport medium, wherein said test tube has an essentially cylindrical shape interrupted by a neck at a predetermined position relative to a level inside the test tube intended to be reached by a free surface of transport medium in gel form wherein said neck comprises a downwards taper of conical shape from a cylindrical section of said test tube and wherein said neck comprises a change in cylindrical cross-section of the test tube, as determined by a downwards-directed conical taper which defines a separation zone between a longer-radius circular cross-section and an underlying shorter-radius circular cross-section along the longitudinal axis of the test tube, with, from said shorter-radius cross-section, the cross-section of the test tube sharply turning back into the initial, longer-radius cross-section on a perpendicular plane to the longitudinal axis of said test tube.

\* \* \* \* \*